(12) United States Patent
Siwak

(10) Patent No.: US 9,072,988 B2
(45) Date of Patent: *Jul. 7, 2015

(54) PREFILTER SYSTEM FOR BIOLOGICAL SYSTEMS

(75) Inventor: Martin Siwak, Topsfield, MA (US)

(73) Assignee: EMD Millipore Corporation, Billerica, MA (US)

( * ) Notice: Subject to any disclaimer, the term of this patent is extended or adjusted under 35 U.S.C. 154(b) by 1448 days.

This patent is subject to a terminal disclaimer.

(21) Appl. No.: 12/075,736

(22) Filed: Mar. 13, 2008

(65) Prior Publication Data

US 2008/0164195 A1    Jul. 10, 2008

Related U.S. Application Data

(62) Division of application No. 11/063,477, filed on Feb. 23, 2005, now Pat. No. 7,390,403.

(60) Provisional application No. 60/650,504, filed on Feb. 7, 2005, provisional application No. 60/554,769, filed on Mar. 19, 2004.

(51) Int. Cl.
  *B01D 15/08*    (2006.01)
  *B01D 15/12*    (2006.01)
  (Continued)

(52) U.S. Cl.
  CPC .......... *B01D 15/125* (2013.01); *B01D 15/3804* (2013.01); *B01D 29/41* (2013.01); *B01D 61/16* (2013.01); *B01D 2239/0407* (2013.01); *B01J 20/28028* (2013.01)

(58) Field of Classification Search
  CPC .. B01D 15/125; B01D 15/3804; B01D 29/41; B01D 61/16; B01D 2239/0407; B01J 20/28028
  USPC .............. 210/767, 788, 806, 198.2, 304, 330, 210/331, 348, 502.1, 512.1
  See application file for complete search history.

(56) References Cited

U.S. PATENT DOCUMENTS 2,758,083 A    8/1956    Van Hoel et al.
2,788,901 A    4/1957    Boeddinghaus et al.
(Continued)

FOREIGN PATENT DOCUMENTS

DE    1942543    9/1970
EP    1203774    5/2002
(Continued)

OTHER PUBLICATIONS

Yigzaw, et al., "Exploitation of the Adsorption Properties of Depth Filters to Remove Host Cell Protein Contaminants in Downstream Processing," Presentation: ACS National Meeting, Session on Bioprocess Integration, Mar. 13-17, 2005.
(Continued)

*Primary Examiner* — Ernest G Therkorn
(74) *Attorney, Agent, or Firm* — EDM Millipore Corporation

(57) ABSTRACT

The present invention is to a prefilter for affinity chromatography columns. The prefilter, positioned upstream of the column inlet, reduces the presence of non-specific binding (NSB) species that enter the system, thereby extending the yield, capacity and lifetime of the column. Suitable agents include but are not limited to hydrophobic entities; lipophilic entities; activated carbon; charged cation or anion entities; ligands; particles such as fumed silica, glass, controlled pore glass or derivitized version of each; silica or silicates; and combinations thereof. The material(s) can be incorporated into a variety of media such as fibers, beads, membranes and the like and then incorporated into a variety of device designs including lenticular pads, depth filters, bead containing columns, spiral wound devices, TFF devices and the like.

4 Claims, 9 Drawing Sheets

(51) Int. Cl.
*B01D 15/38* (2006.01)
*B01D 29/41* (2006.01)
*B01D 61/16* (2006.01)
*B01J 20/28* (2006.01)

(56) References Cited

U.S. PATENT DOCUMENTS

| | | | |
|---|---|---|---|
| 3,241,678 A | 3/1966 | Wrontnowski |
| 3,647,084 A | 3/1972 | Martin |
| 3,976,576 A | 8/1976 | Jacobsn et al. |
| 4,007,113 A | 2/1977 | Ostreicher |
| 4,007,114 A | 2/1977 | Ostreicher |
| 4,016,081 A | 4/1977 | Martinez et al. |
| 4,228,015 A | 10/1980 | De Vries et al. |
| 4,310,416 A | 1/1982 | Tanaka et al. |
| 4,704,207 A | 11/1987 | Chu |
| 4,783,262 A | 11/1988 | Ostreicher et al. |
| 4,895,806 A | 1/1990 | Le et al. |
| 5,059,654 A | 10/1991 | Hou et al. |
| 5,069,791 A | 12/1991 | Becker et al. |
| 5,085,784 A | 2/1992 | Ostreicher |
| 5,429,742 A | 7/1995 | Guttman et al. |
| 5,490,926 A | 2/1996 | Hammaken |
| 5,614,105 A | 3/1997 | Heilmann et al. |
| 5,681,464 A | 10/1997 | Larsson |
| 5,766,472 A | 6/1998 | Tzakis |
| 5,853,445 A | 12/1998 | Wong et al. |
| 5,922,200 A | 7/1999 | Pearl et al. |
| 5,928,588 A | 7/1999 | Chen et al. |
| 5,965,019 A | 10/1999 | Olsen et al. |
| 6,365,395 B1 | 4/2002 | Antoniou |
| 6,524,513 B1 | 2/2003 | Pearl et al. |
| 6,827,851 B1 | 12/2004 | Strohm et al. |
| 7,118,675 B2 | 10/2006 | Siwak et al. |
| 7,390,403 B2 * | 6/2008 | Siwak ................... 210/198.2 |
| 2003/0201229 A1 | 10/2003 | Siwak et al. |
| 2004/0188339 A1 | 9/2004 | Murkute et al. |

FOREIGN PATENT DOCUMENTS

| | | |
|---|---|---|
| GB | 1234283 | 6/1971 |
| GB | 1494827 | 12/1974 |
| GB | 2013522 | 8/1979 |
| GB | 2063089 | 6/1981 |
| JP | 62-168511 A | 7/1987 |
| JP | 64-4210 A | 1/1989 |
| JP | 4-504379 A | 8/1992 |
| JP | 7-133289 A | 5/1995 |
| JP | 09-510200 A | 10/1997 |
| JP | 9-510200 A | 10/1997 |
| JP | 2001-513419 A | 9/2001 |
| JP | 2003-12693 A | 1/2003 |
| WO | 90/11814 A1 | 10/1990 |
| WO | 95/24418 A1 | 9/1995 |
| WO | WO 01/83077 | 11/2001 |
| WO | 03/040166 A2 | 5/2003 |
| WO | WO 03/066669 | 8/2003 |
| WO | WO03/086576 | 10/2003 |
| WO | WO2005/007266 | 1/2005 |

OTHER PUBLICATIONS

European Search Report, EP 1577319, Jul. 4, 2005, pp. 17-18.
European Search Report, EP 1609517, Jul. 13, 2005, pp. 14-15.

\* cited by examiner

PREFILTER SYSTEM FOR BIOLOGICAL SYSTEMS

CROSS REFERENCE RELATED APPLICATIONS

This application is a divisional patent application of U.S. patent application Ser. No. 11/063,477 filed on Feb. 23, 2005; which claims the benefit of U.S. Provisional Application No. 60/650,504, filed on Feb. 7, 2005 now U.S. Pat. No. 7,390,403; and of U.S. Provisional Application No. 60/554,769, filed on Mar. 19, 2004.

BACKGROUND OF THE INVENTION

In the purification of biological streams, the goal is to capture one or more desired proteins from a liquid stream that contains a variety of components such as other proteins, lipids, aggregated proteins from the cells, media proteins, carbohydrates and colloids from cell walls, DNA, DNA/protein complexes and the like. A number of purification steps may be used but general revolve around one or both of affinity chromatography and ultrafiltration (UF) systems.

The liquid stream is generally derived from a batch of lysed cells that have been engineered to produce the desired protein. Most of the cell components are removed from the liquid by filtration or centrifugation before chromatography and/or ultrafiltration. However a surprisingly large amount, especially of small or soluble constituents remain in the liquid as it is applied to the purification system. Many of these compete with the desired protein and bind to the affinity material in the column or clog the ultrafilter.

In affinity chromatography, some of the constituents bind preferentially so over that of the desired protein reducing yields. Others irreversibly bind to the affinity material reducing not only yields but overall capacity especially on subsequent uses of the media.

Most of these non-desired species are known as non-specific binding species and the problem has been called non-specific binding (NSB).

Various methods have been attempted to reduce NSB, both to increase yield initially and to maintain capacity over time for a column and to maintain a desired rate of flux and extend the useful life of a UF system.

Generally, a column is washed several times between the affinity capture stage and the elution stage with various buffers at different pHs and/or with different chemical washes in an attempt to remove the NSB species. Likewise the use of various cleaning regiments have been employed after use to try and remove as much of the NSB species from the media as possible to maintain yield and capacity values.

None of these have proven to greatly effective especially with the most commonly used affinity media in the biopharmaceutical industry. In part this is due to the affinity ligand itself Protein A. It being a protein is susceptible to denaturing under various conditions that other wise could be used to reduce NSB such as heat, high caustic concentrations and the like.

UF systems are cleaned after the system has become plugged enough to create too high a back pressure or to reduce the flux below a given level. Its filters are then cleaned with caustic solutions before reuse.

While the washing with caustic often results in a membrane free of NSB species, it does nothing to extending the life of a filter during filtration. The problem of fouling still exists.

What is needed is a means for reducing NSB to a lower level before the liquid ever reaches the purification step. The present invention provides such an invention.

SUMMARY OF THE INVENTION

The present invention relates to a prefilter for purification systems of biological products such as monoclonal antibodies. More particularly it relates to a prefilter for removing non-specific binding (NSB) constituents from a liquid stream before being applied to a purification systems such as an affinity chromatography column or ultrafiltration system.

The present invention is to a prefilter for purification systems such as UF systems and affinity chromatography columns. The prefilter reduces the presence of NSB species that enter the system, thereby extending the yield, capacity and lifetime of the affinity media used in the column and reducing the fouling of the UF membranes. Suitable agents include but are not limited to hydrophobic entities; lipophilic entities; activated carbon; charged cation or anion entities such as ion exchange beads or powders; ligands; particles such as fumed silica, controlled pore glass or derivitized version of each; silica or silicates; and combinations thereof.

The media can be used as is in a column if desired or it can be incorporated into another filter media. Various filter forms such as packed beds, lenticular pads, depth filters, pleated filters and the like can be used.

A preferred prefilter is in the form of one or more lenticular filtration pad devices, each containing a fibrous media and one or more NSB agents. One such device is a lenticular pad formed of one or more layers of fibrous material containing a NSB agent formed of glass or silica particles embedded in the fibrous material. Another is a lenticular device formed of a series of glass mats. A preferred device is a lenticular pad formed of one or more layers of cellulosic material containing a NSB agent formed of controlled pore glass particles embedded in the fibrous material.

Another preferred form is as a spiral wound filter cartridge. One or more layers of a fibrous material containing one or more of the NSB agents can be wound around themselves or a central mandrel as is well known in the art.

Another preferred form is as a disposable capsule containing a series of flat disks of a fibrous material containing one or more NSB agents with the disks having a central bore and a series of inner and outer knife edge seals forming a fluid pathway such that all fluid exiting the device must first flow through the disks.

A further preferred embodiment is in the form of a tangential flow device with fibrous material containing one or more NSB agents arranged in a series of cassettes or pods with the flow running across or tangential to the material and at least a portion of the fluid passing through the material on each pass.

It is an object of the present invention to provide a prefilter for a protein purification system comprising one or more layers of one or more media selected to remove non-specific binding constituents from a protein containing stream.

It is an object of the present invention to provide a protein purification system comprising a protein purification system having an inlet and an outlet and a space between wherein the space is filled with media for the purification of proteins and a prefilter upstream of and connected to the inlet of the system, said prefilter comprising one or more layers of one or more media selected to remove non-specific binding constituents from a protein containing stream.

It is an object of the present invention to provide a protein purification system comprising a protein purification system having an inlet and an outlet and a space between wherein the space is filled with media for the purification of proteins and a prefilter upstream of and connected to the inlet of the system, said prefilter comprising one or more layers of one or more media selected to remove non-specific binding constituents from a protein containing stream and a storage tank in fluid communication with the outlet of the prefilter and the inlet of the purification system.

It is an object of the present invention to provide a prefilter system for an affinity chromatography column comprising one or more prefilters in the form of one or more lenticular pad devices, each device having a central lenticular support structure, one or more prefilter pads, each pad being formed of one or more layers of one or more media selected to remove non-specific binding constituents from a protein containing stream, an edge seal securing the one or more pads to the support and a central outlet such that all fluid entering the device must pass through the one or more prefilter pads and the support before reaching the central outlet and a housing in which the one or more prefilters are arranged, the housing having a central rod on to which each device is mounted by its central outlet the central rod being connected to an outlet of the housing, a space between the devices and the inner wall of the housing for fluid flow and an inlet in the housing.

It is another object to provide a prefilter for an affinity chromatography column comprising one or more layers of one or more media selected to remove non-specific binding constituents from a protein containing stream wherein the prefilter is in the form of one or more lenticular pad devices, each device having a central lenticular support structure, one or more prefilter pads, an edge seal securing the pads to the support and a central outlet such that all fluid entering the device must pass through the one or more prefilter pads and the support before reaching the central outlet.

DETAILED DESCRIPTION OF THE INVENTION

Figure 1A:
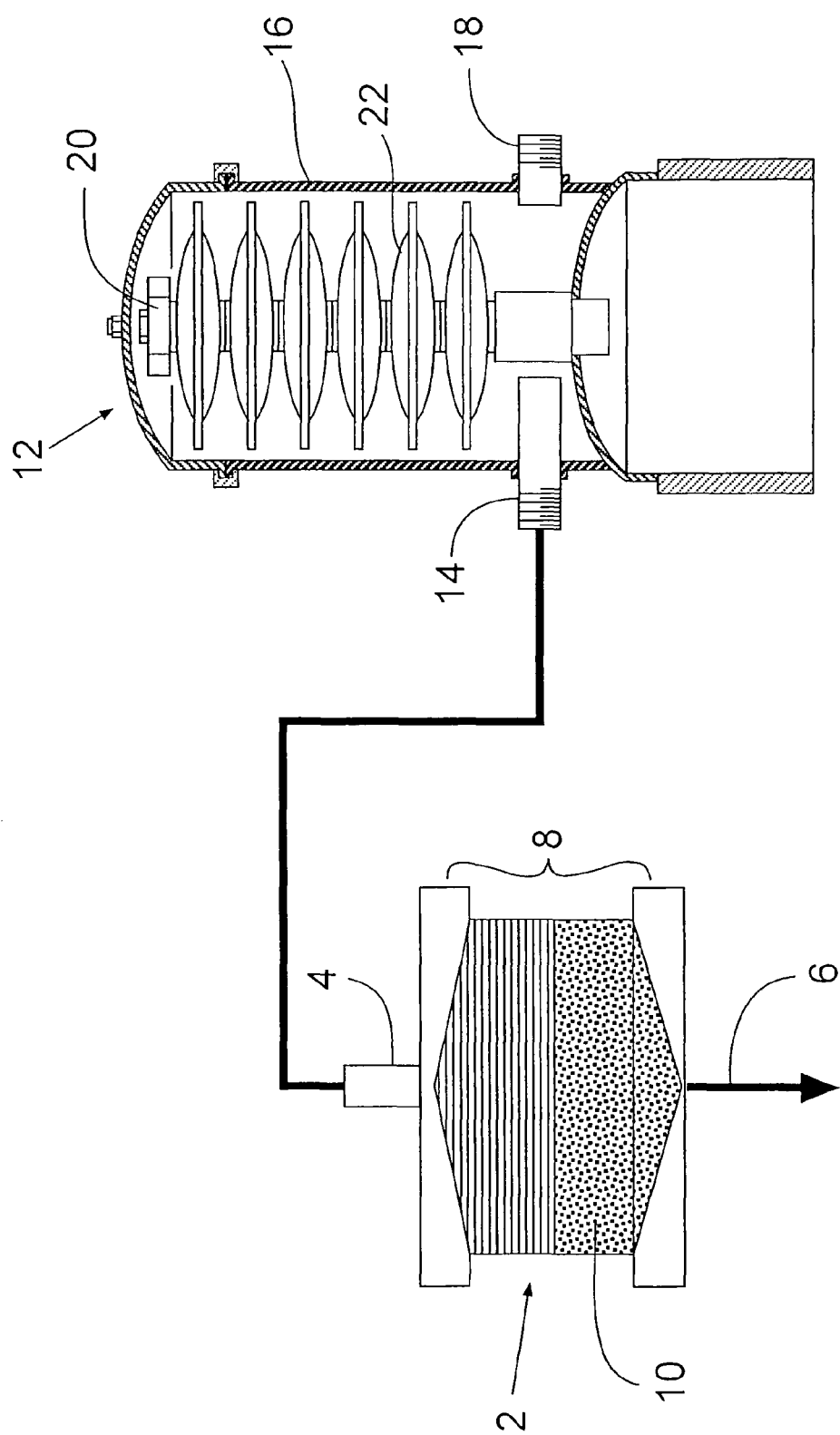
FIG. 1A shows a first embodiment of the present invention in cross-sectional view.

The present invention is a prefilter used upstream of a protein purification systems an affinity media containing chromatography column or UF system to remove some or all of the NSB species before they reach the purification system. In this way, the amount of NSB is reduced and media has higher yields and capacity and a longer life than is achieved today.

The prefilter contains one or more types of materials that are capable of removing the NSB species from the liquid. In this way, the amount of NSB species reaching the column is reduced or eliminated, making their competition for binding sites less or non-existent. This leads to several advantages and benefits. For chromatography systems, one achieves higher overall capacity for the desired species that are to be captured, higher yields of the desired species as more of that species will have binding sites available for it to be captured upon with the reduced load of NSB species and greater retained capacity over time as less irreversible binding of NSB species will occur allowing the chromatography media to be cleaned and reused to a greater degree than is possible today. For UF systems one reduces fouling and extends the filtration run life before it needs to be cleaned or replaced.

The NSB removing material used in the prefilter can be any material shown to remove the NSB specie or species that are desired to be removed from the liquid stream before chromatographic separation. Typically, these materials are selected from the group consisting of hydrophobic entities, lipophilic entities, activated carbon, charged cation or anion entities such as ion exchange beads, ligands, particles such as silica, silicates, fumed silica, controlled pore glass or derivitized version of each, and combinations thereof.

These materials may be incorporated into a media, preferably a porous media that can then be incorporated into a selected device design. Such media can be in the form of films, porous films, membranes, porous mats, porous monoliths, nonwovens, woven fabrics and the like.

They can be formed of a wide variety of materials as are used by one of ordinary skill in the art of filtration such as polyolefins including polyethylene and polypropylene, polyvinyl alcohols, polyvinyl chlorides, polysulfones, polyarylsulfones, polyethersulfones, polyphenylsulphones, PTFE, PFA resins, polyesters, nylons, polyamides, polyimides, PVDF, celluloses and modified cellulosic materials such as cellulose acetate, ceramics, glass such as borosilicate glass or controlled pore glass and the like.

The form of the NSB removing material will dictate whether and if so how it is incorporated into the selected media. For example, ligands can be attached by surface chemistry to a substrate such as controlled pore glass. Activated carbon, silica, controlled pore glass and the like can be in the form of particles such as beads and added as a filler to the media as it is being formed. One example is to add the NSB removing material as a filler to PTFE resin and compound the two together to obtain a porous membrane of PTFE containing the filler of NSB removing material dispersed throughout the fibrous PTFE structure. Some materials, such as beads of activated carbon, silica, controlled pore glass are self supportive and do not need to be incorporated into a media. Instead they can be used as is in a bed of such material. However they can easily be incorporated into a media as a filler if desired.

A prefilter according to the present invention can be formed of a variety of materials and in a variety of device designs.

FIG. 1A shows a first embodiment of the present invention. A chromatography column 2 has an inlet 4 and an outlet 6 and a space 8 in between the inlet 4 and outlet 6. The space 8 is filled with one or more types of affinity media 10 such as Protein A or Protein G ligands, or chemical ligands such as 2-aminobenzimidazole (ABI), aminomethylbenzimidazole (AMBI), mercaptoethylpyridine (MEP) or mercaptobenzimidazole (MBI) attached to a chromatographic bead such as agarose, silica or controlled pore glass. Such affinity media are well known in the art and can be obtained for example from Millipore Corporation under the tradename ProSep®A media (Protein A based ligand on controlled pore glass) or ProSep®G media (Protein G based ligand on controlled pore glass).

A prefilter assembly 12 is located upstream of the column 2 such that the outlet 14 of the prefilter assembly 12 is in fluid communication with the inlet 4 of the column 2. The assembly 12 is comprised of a housing 16 having the outlet 14 and an inlet 18, a central rod assembly 20 connected to the outlet 14 and a series of prefilters 22 arranged about the rod 20 in a liquid tight fashion to the rod 20, each other 22 and within themselves 22 so that all fluid exiting the outlet 14 had to first enter the inlet 18, pass through one of the prefilters 22 to the rod 20 and then to the outlet 14.

Figure 1B:
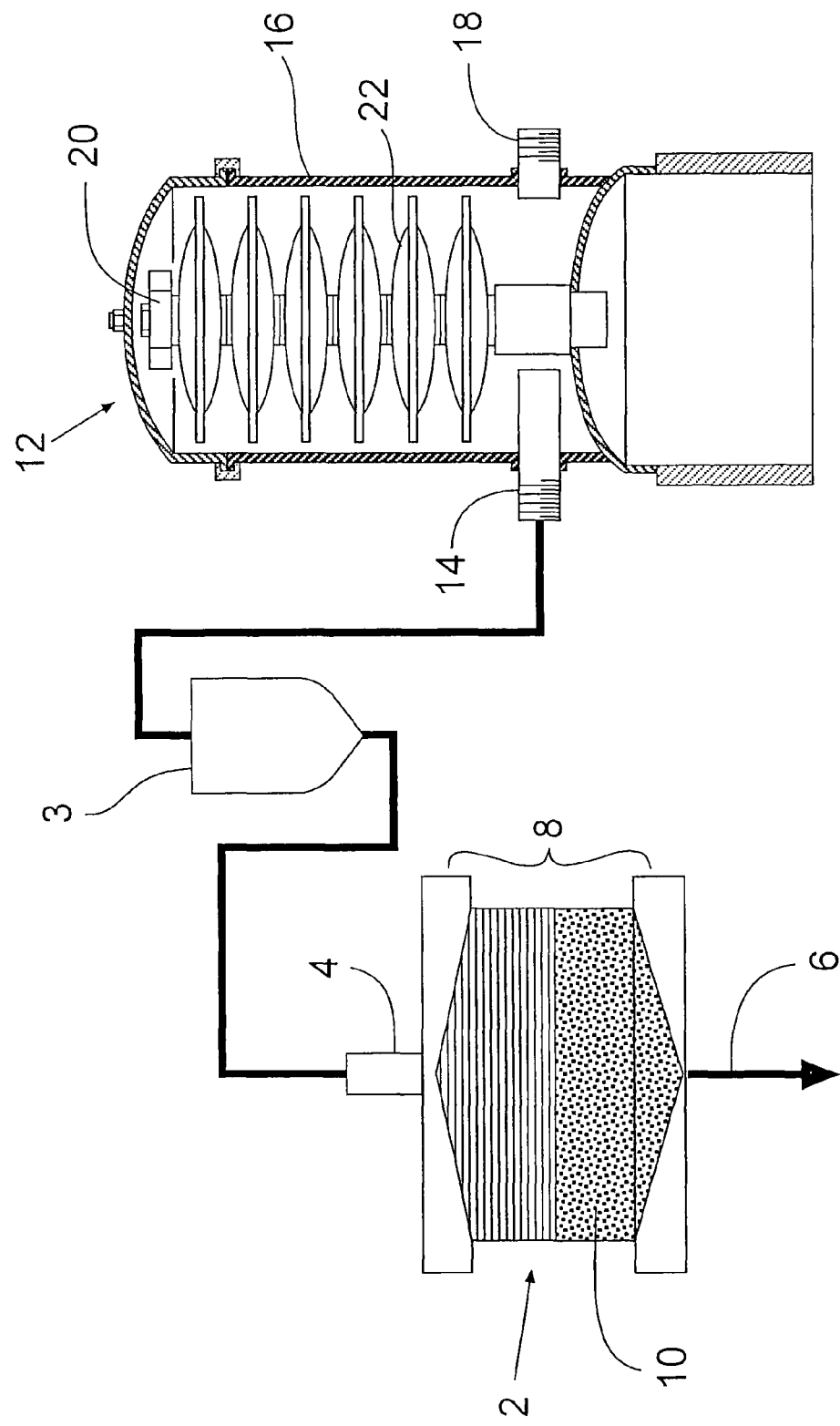
FIG. 1B shows a second embodiment of the present invention in cross-sectional view.
Figure 1C:
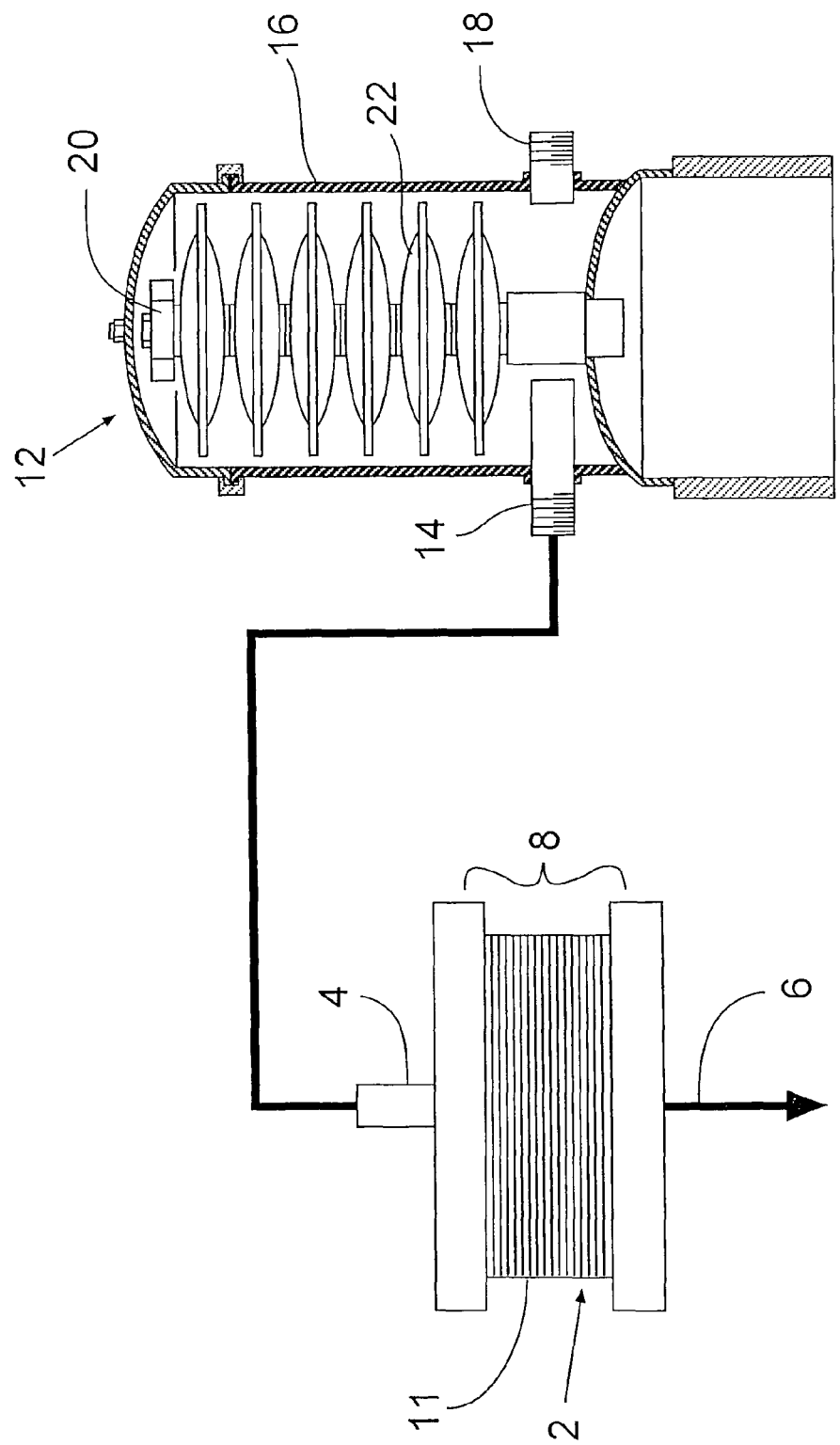
FIG. 1C shows a third embodiment of the present invention in cross-sectional view.
Figure 2:
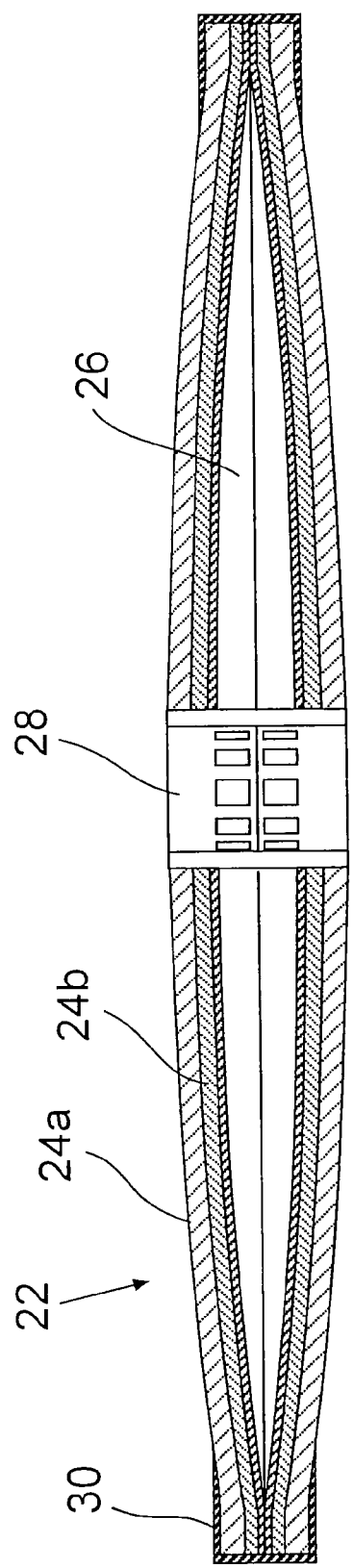
FIG. 2 shows a prefilter of one embodiment of the present invention in cross-sectional view.

FIG. 2 shows an alternative embodiment of FIG. 1 in which an intermediate storage tank 3 is positioned between the prefilter 12 and the column 2. The tank can be used to store the treated fluid before it goes onto the column so that the either the prefilter or the column or both can be run in a batch mode rather than in a continuous mode if desired.

Figure 3:
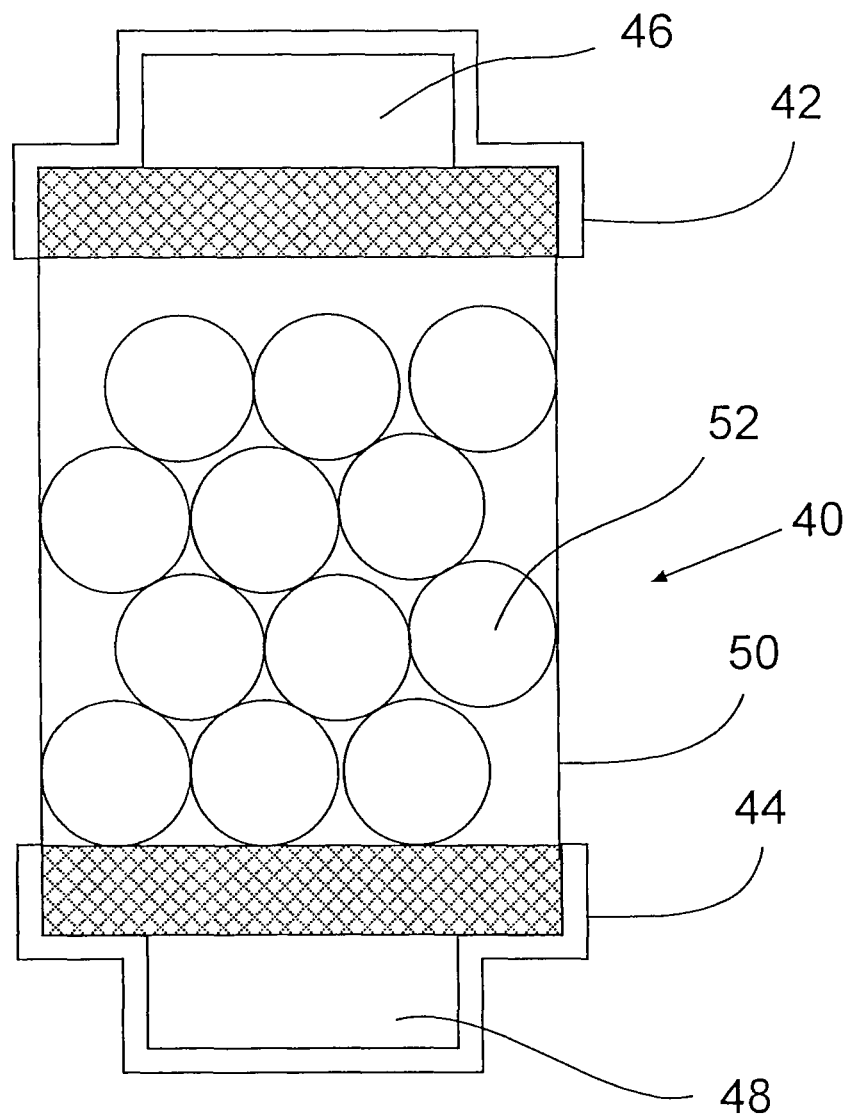
FIG. 3 shows a prefilter of one embodiment of the present invention in cross-sectional view.

FIG. 3 shows an alternative embodiment of FIG. 1 in which an ultrafiltration device 5, such as a tangential flow device such as a PELLICON® TFF system available from Millipore Corporation of Billerica, Mass. is used instead of the column. It contains one or more layers of ultrafiltration membrane 11 with or without various spacers, feed screens, filtrate screen sand the like. If desired to run this embodiment in a batch mode, one can use a tank as shown in FIG. 1B (not shown in FIG. 1C).

Other additional elements may be added to the embodiments of FIGS. 1A-1C such as one or more pumps, valves, pressure gauges, temperature sensors or controls, sampling ports, and the like as are commonly used in the biopharmaceutical industry.

The prefilters 22 of FIGS. 1A-C are shown in more detail in FIG. 2 are made as supported cells with the one or more layers of porous media, in this case two layers 24A and B being attached to the outer surfaces of a central support device 26. The supported cells are formed on a lenticular (double convex) support structure formed of a series of radially extending convex shaped ribs (not shown) which are held to each other by a series of spaced rings (Not shown) at various circumferences from the center of the radial ribs. See U.S. Pat. Nos. 4,704,207 and 4,783,262. The spaces between the ribs form the channels through which fluid that has flowed through the filter media is collected and sent to the core 28 for further use. The rings are arranged in a manner so that the fluid flow is only minimally hindered. Typically, adjacent rings are formed on opposite sides of the ribs so that flow is over one ring and then under the other. The outer edge of the media is liquid tightly secured by an outer sealing edge 30.

The prefilters may be used singularly or in groups. See U.S. Pat. Nos. 2,788,901 and 5,085,784. Typically the prefilters are used in groups (generally of 16 to 20 per group) stacked upon a central rod within a housing as shown in FIG. 1. Fluid to be filtered enters the bottom or side adjacent the bottom of the housing and flows through the filter media to the lenticular support structure that direct the fluid to the core where it is collected and removed from the housing through an outlet in the bottom or side of the housing.

In a preferred embodiment of this design, the filter includes multiple layers of media. Such multiple layers may also be different materials and/or different pore sizes. Preferably, each such media has different pore size ranges, so a great variety of different cartridges can be made from the present invention. These media can be obtained from a variety of sources such as MILLISTAK+™ media available from Millipore Corporation of Bedford, Mass. Filter Materials of Waupaca, Wis. also produces a wide array of media suitable for the device of the present invention.

Representative media useful for forming the filter include the fiber of polyolefins such as polyethylene, polypropylene, cellulose including cellulose/silica blends as well as cellulose derivatives such as cellulose acetate, cotton, polyamides, polyesters, fiberglass, polytetrafluoroethylene (PTFE), fluoropolymers such as PFA, MFA and FEP or the like. Celluosic media or cellulosic composite media are preferred such as the MILLISTAK+™ filters available from Millipore Corporation of Billerica, Mass. These materials and their methods of making them either by a wet process (similar to papermaking) or a dry process are well known in the art, See U.S. Pat. Nos. 5,928,588 and 4,007,113 and 4,007,114 for examples of making such media.

Similar materials are appropriate for the structural portions of the cartridge. Preferably, they are made of polypropylene. Other materials suitable for use in these applications can include but are not limited to thermoplastics such as other polyolefins such as polyethylenes including ultrahigh molecular weight polyethylenes, copolymers or terpolymers of polyolefins; nylons; PTFE resin, PFA, PVDF, ECTFE, and other fluorinated resins, particularly perfluorinated thermoplastic resins; polycarbonates; metallocene derived polymers, polysulphones; modified polysulphones such as polyethersulphone, polyarylsulphones or polyphenylsulphones; any glass or other reinforced plastic; or a metal such as stainless steel, aluminum, copper, bronze, brass, nickel, chromium or titanium or alloys or blends thereof.

In a second embodiment of the present invention, one uses a column of packed NSB removing material. Such a device is shown in FIG. 3. In this embodiment, a column 40 has a top cover 42 and a bottom cover 44, the top cover 42 having an inlet 46 and the bottom cover 44 having an outlet 48. Both the inlet 46 and outlet 48 are separated from the body 50 of the column 40 by one or more porous devices such as frits, membranes, screens, distributors and the like that control the distribution of the fluid into and out of the column 40 and also prevent movement of the NSB removing materials 52 out of the column 40. Such devices are well known and can be formed of sintered plastics such as sintered polyethylene, sintered metals such as sintered stainless steel or nickel, a glass mat or mesh, a plastic mat, netting or mesh such as a polyethylene nonwoven mat and the like.

In this embodiment, the NSB removing materials 52 are shown as particles. They can be in the form of regular beads, irregular particles, shards, fibers, monoliths or any other form in which they are normally supplied. Such particle-based materials include but are not limited to silica, silicates, controlled pore glass, and derivitized versions of any of the above as well as activated carbon beads. The column may contain a single type of NSB removing material or if desired it may contain either a blend of different NSB removing materials or a series of different NSB removing materials in individual layers within the column. The particles can be of any size normally used in bead based filtration, but typically are from about 10 to about 1000 microns in average diameter. To ensure even flow with low back pressure, it is preferred that the particles are of substantially the same size, generally about 50% or more of the particles are +/−10% the average diameter. In some instances they can be monodispersed particles, at least 90% are +/−10% the average diameter.

Figure 4:
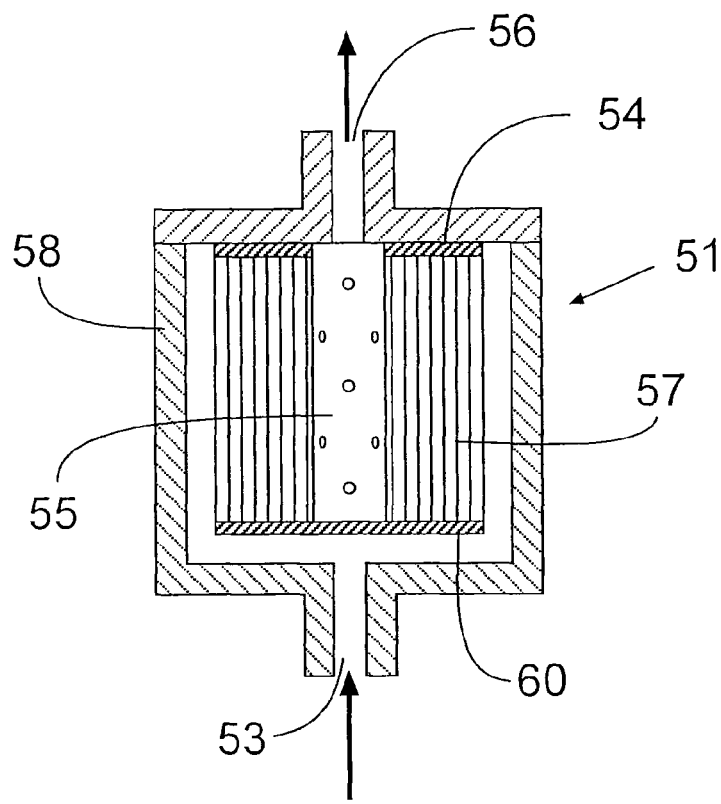
FIG. 4 shows a prefilter of one embodiment of the present invention in cross-sectional view.

The NSB removing material may also be incorporated into a filter cartridge device as in FIG. 4 either as a pleated filter or as a depth filter. In this embodiment, the NSB removing material is incorporated into a porous support media such as a nonwoven of PTFE or polyethylene, a cellulosic fibrous pad as in FIG. 1 or a porous plastic membrane, each of which contain the NSB removing material either as a filler or as an attached chemistry as in the case of the ligands. A cartridge 51 contains a central core 55 that is connected to a first endcap 54 which forms an outlet 56 from the cartridge 51. The NSB removing material containing media 57 is upstream from the core 55. If desired a support layer or cage (not shown) may be used either on the outside or inside or both sides of the media 57 as is well known in the art. The media 57 is liquid tightly sealed to the first endcap 54 and a second endcap 60 at its respective ends so that all fluid entering the cartridge 51 through inlet 53 must flow through the media 57 before entering the core 55. An outer sleeve 58 surrounds the media 57 and is also sealed to the endcap 54 such as by mated threads, clamps, adhesives, solvent bonding, ultrasonic welding and the like. In the pleated form, one or more layers of media may be used. Likewise in the depth filter form the media maybe one thick layer, such as a mat or a felt or a monolith or it may be a single sheet of media that has been rolled up upon itself or it may be series of individual sheets on top of each other and sealed along their open two edges (not shown). The cartridge may go into a reusable housing that is liquid tight or it may have the outer sleeve liquid tight (as shown) so that the cartridge is in the form of a disposable capsule cartridge.

Figure 5:
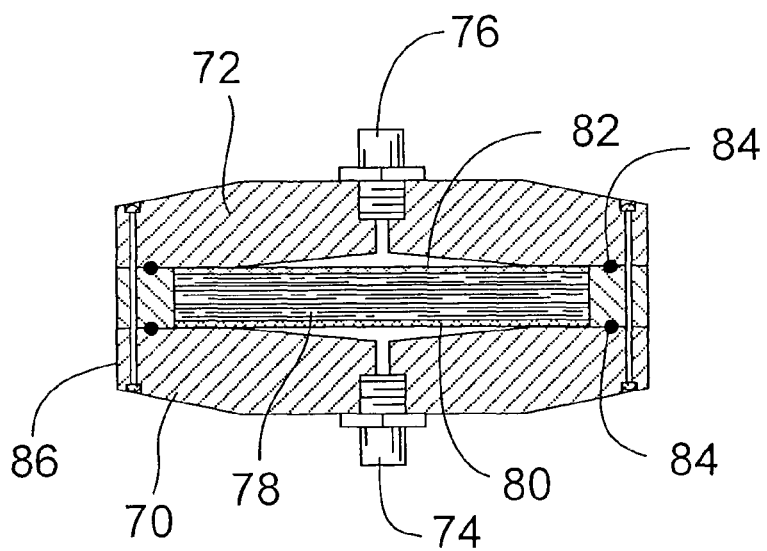
FIG. 5 shows a prefilter of one embodiment of the present invention in cross-sectional view.

FIG. 5 shows another device embodiment. In this embodiment as well, the NSB removing material is incorporated into a porous support media such as a nonwoven of PTFE or polyethylene, a cellulosic fibrous pad as in FIG. 1 or a porous plastic membrane that contain the NSB removing material either as a filler or as an attached chemistry in the case of the ligands. This design is also shown in U.S. Pat. No. 4,895,806 and consist of two halves, 70 and 72, the first half 70 having an inlet 74 and the second half 72 having an outlet 76. Inside the device are a plurality of media discs 78 stacked one on top of the other between a top and bottom porous substrate 80 and 82 respectively. Sealing around the circumference of the discs and the top and bottom of the stack of discs is provided by a series of gaskets 84.

Figure 6:
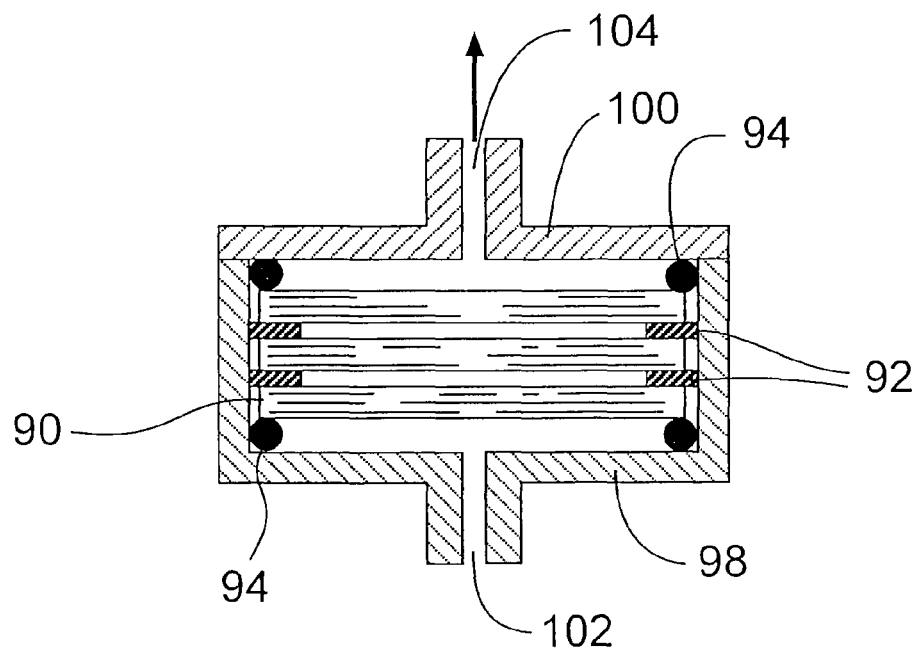
FIG. 6 shows a prefilter of one embodiment of the present invention in cross-sectional view.

FIG. 6 shows a variation on the design of FIG. 5 in which a series of media layers 90 are separated from each other by spacers 92 and are all liquid tightly sealed around the top and bottom circumferences of series of media layers 90 to the interior of the device by gaskets 94. The device is formed of two halves 98 and 100 with an inlet 102 and outlet 104 formed in respective ends of the two halves 98 and 100 of the device.

Figure 7:
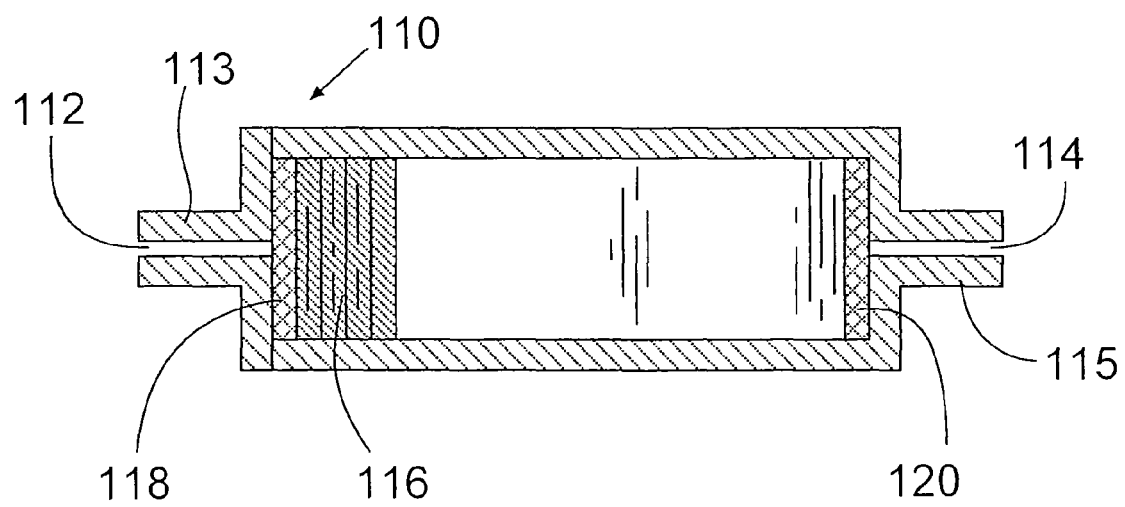
FIG. 7 shows a prefilter of one embodiment of the present invention in cross-sectional view.

FIG. 7 shows another device format formed of a cartridge 110 having an inlet 112 in one end 113 and an outlet 114 in the other end 115 and a series of layers of media 116 in between. Again the NSB removing material is incorporated into a porous support media such as a nonwoven of PTFE or polyethylene, a cellulosic fibrous pad as in FIG. 1 or a porous plastic membrane that contain the NSB removing material either as a filler or as an attached chemistry in the case of the ligands. Porous spacers, 118 and 120 are adjacent the inlet and outlet respectively and maintain the media in place. The media is formed of a size such that the media contacts the inner wall of the device so that all flow must be through the body of media rather than by passing the media along the inner wall or the like.

Other device designs can and are possible with the present invention.

Figure 8:
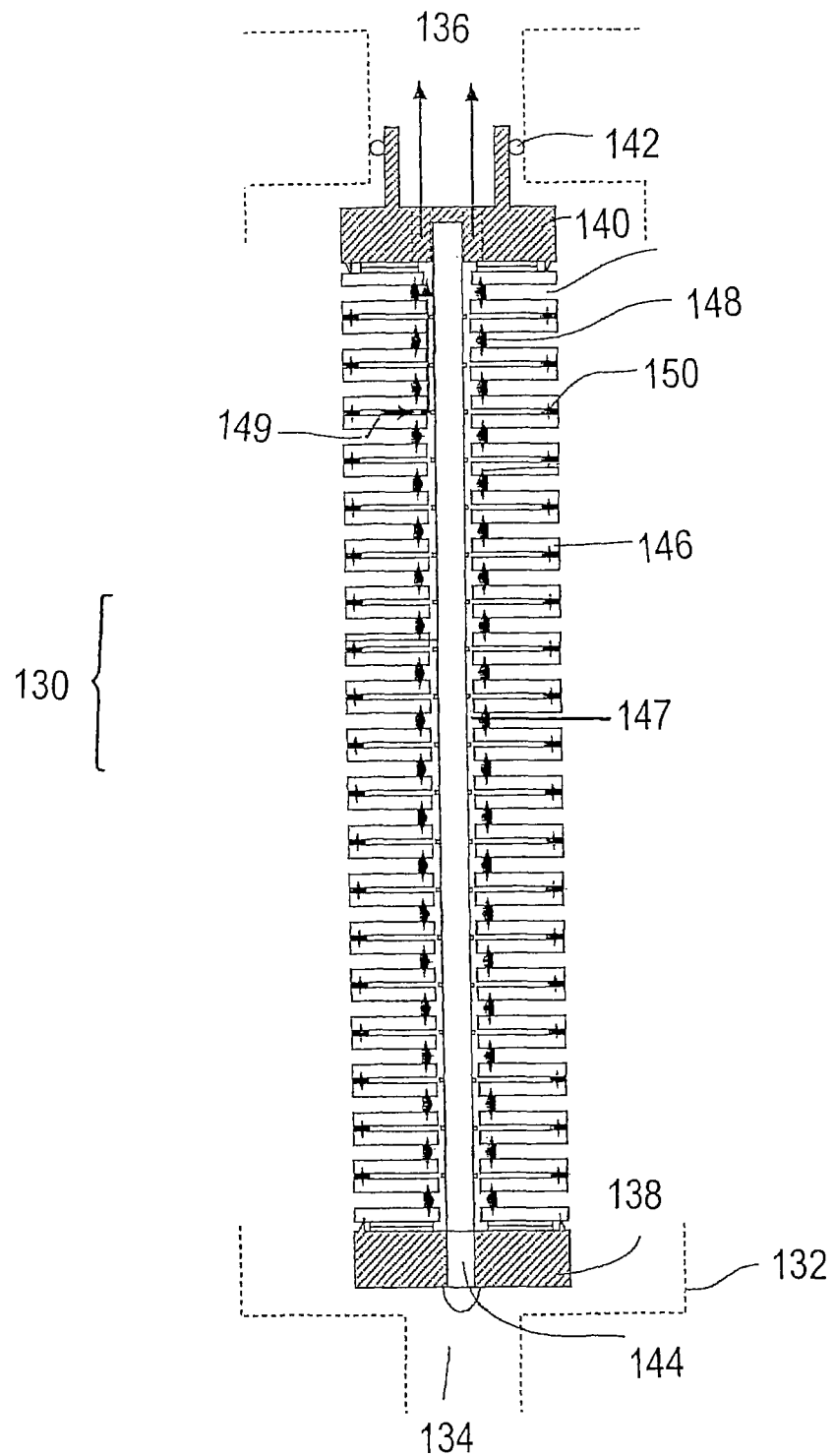
FIG. 8 shows a prefilter of one embodiment of the present invention in cross-sectional view.

For example, FIG. 8 shows the use of a stacked filter device 130 as described in WO 01/83077 A1. The device 130 can be mounted in a housing 132 which can be disposable capsule or a reusable housing. The housing 132 has an inlet 134 and an outlet 136. A first end cap 138 is connected to a second endcap 140 which is in liquid tight communication with the outlet 136. As shown, this is achieved by an O-ring 142 although other means well-known in the art may also be used. A central rod 144 connects the first endcap 138 to the second endcap 140. A series of disks 146 made of the fibrous material containing one or more of the NSB agents are arranged around the central rod 144. This is achieved by each disk having a central bore 147 through which the rod 144 extends. A series of inner 148 and outer 150 knife edge seals are alternatively arranged with the disks 146 to create a series of alternating disk pairs. These seals 148 and 150 seal the respective locations of the disks 146 such that all fluid entering the inlet 134 must pass through one or more of the disks 146 before entering the central bore 147 and then to the outlet 136 as shown by arrow 149. The rod 144 may use a nut or some other means as is well-known in the art to maintain a sealing pressure on the seals 148 and 150 and the disks 146 to ensure that no bypass of liquid occurs.

Figure 9:
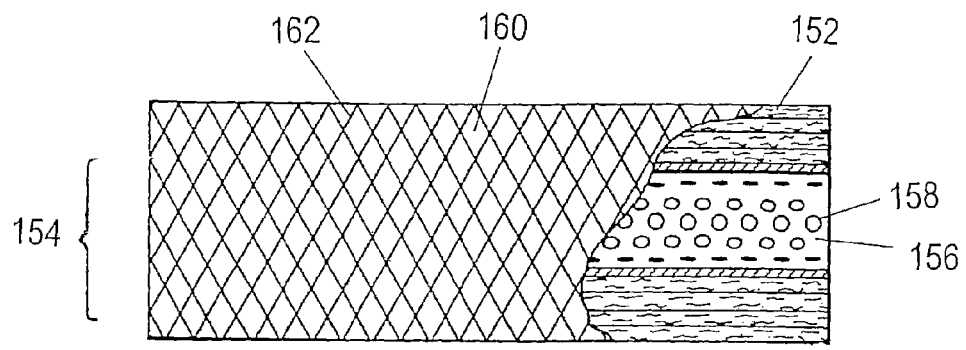
FIG. 9 shows a prefilter of one embodiment of the present invention in cross-sectional view.

FIG. 9 shows another embodiment in which the NSB agent containing material 152 is formed into a spiral wound assembly 154 as is well-known in the art such as from U.S. Pat. No. 5,490,926. The assembly 154 is wound around a permeate collection tube 156 having a series of openings 158 so that fluid passing through the material may enter the tube 156. The outer layer 160 has a protective outer mesh 162 to hold the filter material 152 in place. This is placed into a housing similar to that of FIG. 8 to form a device.

Figure 10:
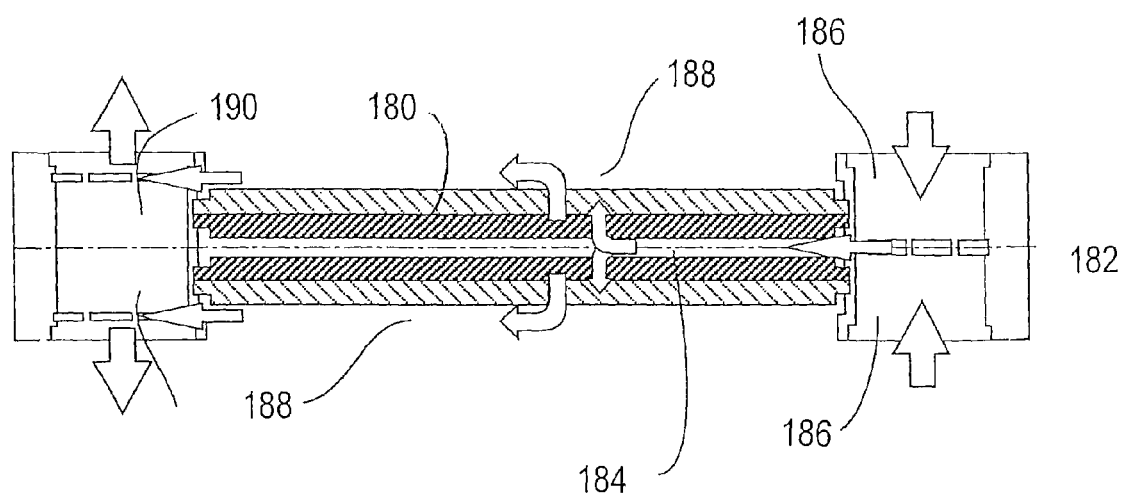
FIG. 10 shows a prefilter of one embodiment of the present invention in cross-sectional view.

FIG. 10 shows another preferred embodiment in which the NSB agent containing material 180 in a tangential flow or TFF device 182. The material 180 is used on both sides of a central portal or distributor 184. Fluid is brought to the distributor by an inlet 186 and fluid then flows into the distributor and through the material 180 to a collection area 188 and then to an outlet 190. Other arrangements can be made such that the fluid flows from the outside to the center or that only a portion of the fluid passes through the filter layer and the remainder is collected from the distributor and recirculated for a second or subsequent pass through the device. This is particularly useful with fluids that contain a high level of impurities that would otherwise clog the device quickly. The tangential flow and recirculation sweeps the filter surfaces clean, reducing the premature clogging of the device.

Other embodiments can be used as well and would be obvious to one of ordinary skill in the art and are meant to be encompassed in the present invention.

What I claim:

1. A tangential flow fluid (TFF) prefilter device for the selective upstream removal of non-specific binding constituents from a fluid stream containing protein during tangential flow fluid filtration, comprising
  an inlet for receiving the protein containing fluid stream being purified;
  a central distributor having two sides and in fluid communication with the inlet;
  one or more layers of porous filter media located on each side of the distributer and in fluid communication with the distributer, each layer of porous filter media having a different pore size range and containing one or more nonspecific binding agents, wherein the nonspecific binding agents are particle-based materials selected from the group consisting of fumed silica, glass, silica, silicates, controlled pore glass, and combinations thereof, a collection area in fluid communication with the porous filter media for receiving the protein containing fluid stream filtered through the media, and an outlet in fluid communication with collection area, such that at least a portion of the protein containing fluid steam passes through the porous filter media on each tangential flow pass.

2. The prefilter device of claim 1, wherein the porous filter media is selected from the group consisting of films, membranes, mats, monoliths, nonwovens, and woven fabrics.

3. The prefilter device of claim 1, wherein the porous filter media is selected from the group consisting of cotton, polyolefins, polyethylene, polypropylene, polyvinyl alcohols, fluoropolymers, polyvinyl chlorides, polysulfones, polyarylsulfones, polyethersulfones, polyphenylsulphones, RIFE, polyesters, nylons, polyamides, polyimides, PVDF, celluloses, modified cellulosic materials, composite cellulosic materials, and cellulose acetate.

4. The prefilter device of claim 1, wherein the wherein the particles is a bead having an average diameter of about 10 to about 1000 microns.

* * * * *

UNITED STATES PATENT AND TRADEMARK OFFICE
CERTIFICATE OF CORRECTION

PATENT NO. : 9,072,988 B2
APPLICATION NO. : 12/075736
DATED : July 7, 2015
INVENTOR(S) : Martin Siwak Page 1 of 1

It is certified that error appears in the above-identified patent and that said Letters Patent is hereby corrected as shown below:

In the Claims

In column 9, line 15, in claim 3 delete "RIFE" and insert -- PTFE --, therefor.

In column 9, line 19, in claim 4 delete "wherein the wherein the" and insert -- wherein the --, therefor.

Signed and Sealed this
Third Day of November, 2015

Michelle K. Lee
*Director of the United States Patent and Trademark Office*